(12) United States Patent
Wise

(10) Patent No.: US 6,835,065 B1
(45) Date of Patent: Dec. 28, 2004

(54) DENTAL IMPRESSION TRAY

(76) Inventor: Thomas B. Wise, 204 Mustang La., Auburn, MI (US) 48611

( * ) Notice: Subject to any disclaimer, the term of this patent is extended or adjusted under 35 U.S.C. 154(b) by 0 days.

(21) Appl. No.: 10/649,466

(22) Filed: Aug. 27, 2003

(51) Int. Cl.[7] .................................................. A61C 9/00
(52) U.S. Cl. ........................................... 433/38; 433/37
(58) Field of Search ............................ 433/37, 38, 41, 433/42, 43, 44, 45, 46, 47

(56) References Cited

U.S. PATENT DOCUMENTS

| | | | |
|---|---|---|---|
| 3,574,259 A | | 4/1971 | Jones |
| D266,269 S | | 9/1982 | Werrin |
| 4,619,610 A | | 10/1986 | Pelerin |
| 4,689,010 A | | 8/1987 | Wolfe |
| D294,062 S | | 2/1988 | Kwok |
| D302,463 S | | 7/1989 | Wolfe |
| 5,316,474 A | | 5/1994 | Robertson |
| 5,513,985 A | | 5/1996 | Robertson |
| 5,636,985 A | | 6/1997 | Simmen et al. |
| 5,702,250 A | | 12/1997 | Kipke |
| 5,733,118 A | | 3/1998 | Pankuch et al. |
| D413,386 S | | 8/1999 | Werrin |
| 6,071,121 A | * | 6/2000 | Simon ........................ 433/37 |
| 6,379,147 B1 | | 4/2002 | Georgakis et al. |
| 6,450,808 B1 | | 9/2002 | Pelerin |
| D464,138 S | | 10/2002 | Werrin |
| D465,574 S | | 11/2002 | Eyde |
| 2002/0064753 A1 | | 5/2002 | Philp, Jr. |
| 2003/0044748 A1 | | 3/2003 | Tucker et al. |
| 2003/0138754 A1 | * | 7/2003 | DiMarino et al. ............ 433/37 |

* cited by examiner

Primary Examiner—Cary E. O'Connor
(74) Attorney, Agent, or Firm—John K. McCulloch

(57) ABSTRACT

A dental impression tray for obtaining an impression of a patient's dentition has a pair of spaced apart limbs spanned by a support for impression material. Each limb has a buccal wall that extends beyond the level of the support and a lingual row of spaced apart projections which also extend beyond the level of the support. Between the buccal wall and the adjacent row of projections is a web pierced by a plurality of openings. The impression material support is a mesh having openings therethrough. The buccal wall, the upstanding projections, the openings in the web, and the openings in the mesh provide an interlock between the dental impression material and the tray which restrains relative movement between the latter and the impression material during the forming of an impression of the patient's dentition.

21 Claims, 2 Drawing Sheets

DENTAL IMPRESSION TRAY

This invention relates to a tray for supporting dental impression material during the making of an impression of a patient's dentition.

BACKGROUND OF THE INVENTION

Impressions of patients' dentitions are produced for a variety of purposes among which are procedures for the manufacture of appliances for bite registrations, crown and bridge constructions, and the like. There generally are five types of impression supporting trays used by a dentist for specific applications. These trays are the posterior, anterior, full arch, quadrant, and sideless posterior. The tray is used simply as a carrier for the impression-forming material and to facilitate the placing and removal of the impression material in and from a patient's mouth.

In use, the tray is filled with a pliable, uncured putty or silicone impression material and seated in a patient's mouth until the material sets or cures. Within a few minutes' time the material will set, but remain pliable and not distort when removed from the patient's mouth.

When the tray containing the impression material is removed from the patient's mouth an accurate negative impression of the tooth or teeth requiring the performance of a dental procedure is completed. The negative impression is used to form an accurate duplicate of the patient's dentition, following which a dental appliance may be produced on a stone model.

Although many different kinds of impression trays are available, not all of them enable good quality dental appliances to be produced. The reasons for this are several, including distortion of the tray due to inadequate rigidity either during the placing of the impression material on the tray or the placing of the tray in the mouth of a patient. Further, other failures of dental appliances are due to the impression material pulling away from the tray borders.

A principal object of the invention is to provide a dental impression tray which overcomes or greatly minimizes the disadvantages referred to above.

SUMMARY OF THE INVENTION

A dental impression tray constructed in accordance with one embodiment of the invention has a generally U-shaped frame having two substantially parallel limbs joined at corresponding ends by a connector. Each limb has a buccal or outer edge and a lingual or inner edge. Adjacent the outer edge of each limb is an upstanding wall. Adjacent the inner edge of each limb is a plurality of upstanding projections spaced from one another and also spaced from the adjacent outer wall. The space between the outer wall and the projections of each limb forms a web. Each web is pierced by a plurality of longitudinally spaced apertures or openings.

In one embodiment the outer wall of each limb extends uniformly in opposite directions from the level of the associated web. The projections associated with each limb also extend in two opposite directions from the level of the web. The height of the projections from the level of the associated web preferably is less than the height of the outer wall.

The connector which joins the corresponding ends of the limbs preferably is thinner than the limbs themselves, thereby facilitating the ability of the dental technician to place a tray in an appropriate position in a patient's mouth.

Spanning the limbs and preferably integrally molded with the latter is a support for dental impression material. The support preferably is of mesh construction having openings therein through which the dental impression material may pass from one side of the support to the other.

In those instances in which the dental practioner wishes to make an impression of both the upper and lower teeth of a patient, the uncured dental impression material may be placed on both sides of the support prior to placing the tray in a patient's mouth. When the tray is placed in the patient's mouth and the patient clinches his jaw to form an impression in the impression material of both the upper and lower teeth, the outer walls will restrict outward movement of the impression material, the projections will restrict inward and longitudinal movements of the impression material, and the openings formed in the web and in the support mesh will provide an interlock between those portions of the impression material on opposite sides of the webs and the support.

In another embodiment of the invention the tray has the limbs, projections, apertures, and impression material support as described above. However, the outer walls and the inner projections extend upwardly from one side only of the limbs.

THE DRAWINGS

A dental impression tray constructed in accordance with the invention is illustrated in the accompanying drawings wherein.

THE PREFERRED EMBODIMENTS

Figure 1:
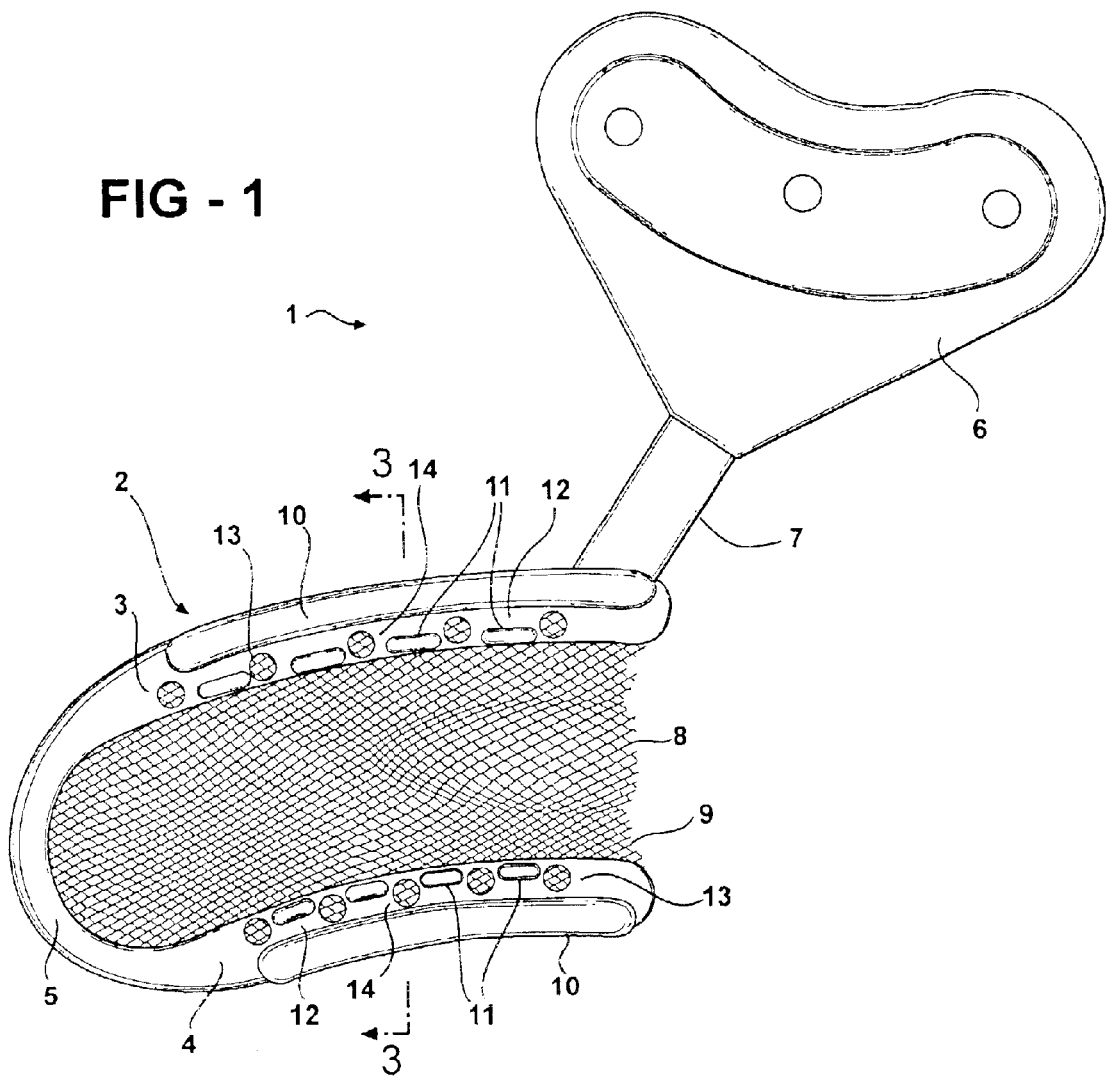
FIG. 1 is a top plan view of one embodiment of a tray.
Figure 2:
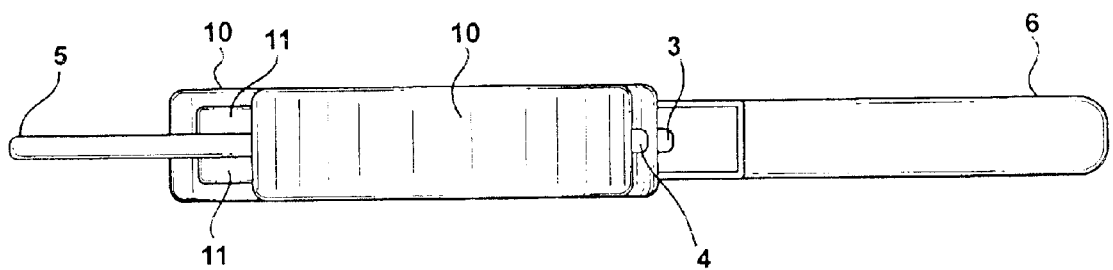
FIG. 2 is a side elevational view.
Figure 3:
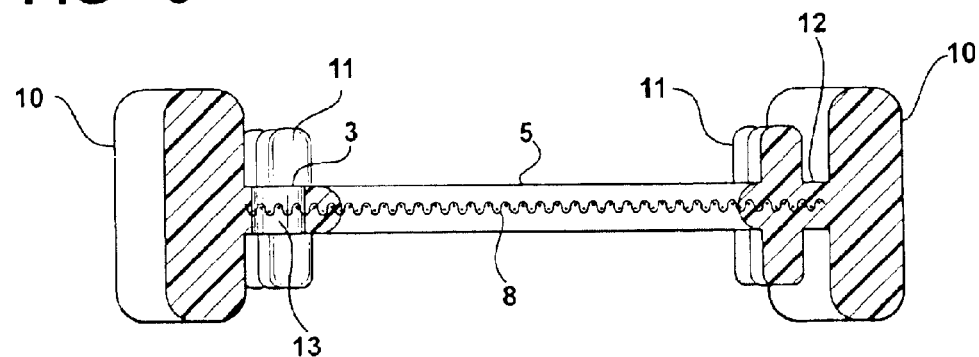
FIG. 3 is a cross sectional view taken on the line 3—3 of FIG. 1.
Figure 4:
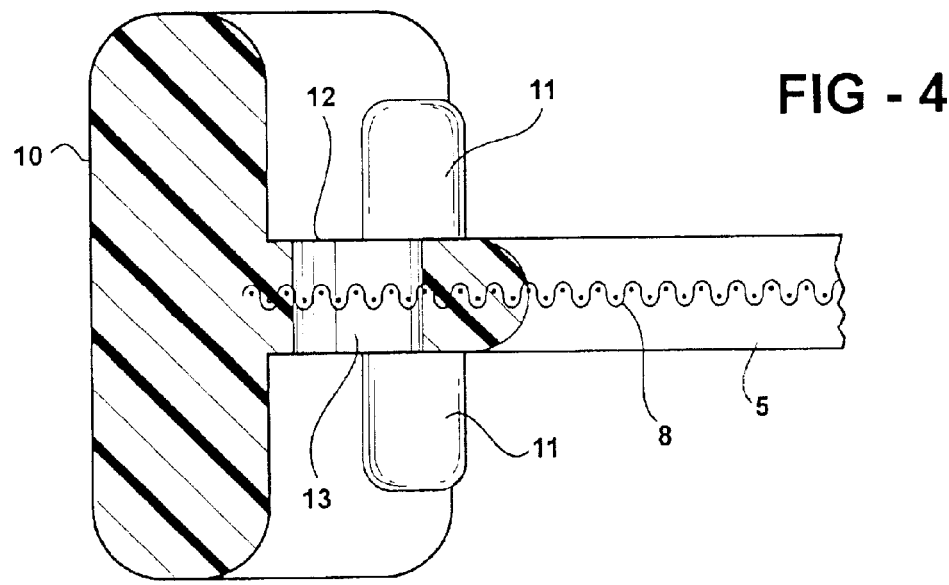
FIG. 4 is an enlarged cross sectional view of one of the limbs shown in FIG. 3.
Figure 5:
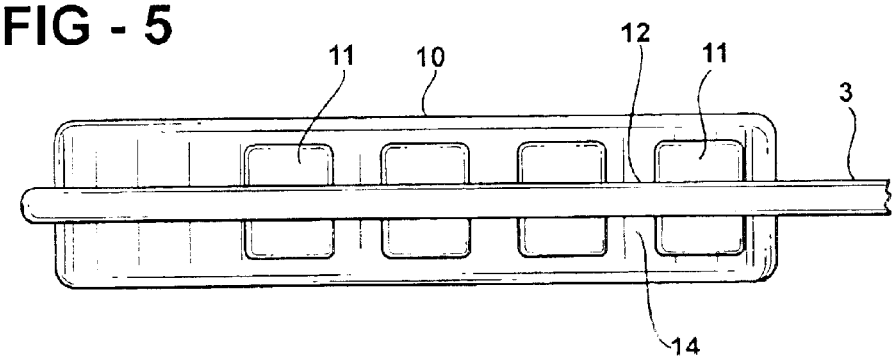
FIG. 5 is a fragmentary elevational view of a portion of one of the limbs.

A tray constructed in accordance with the embodiment shown in FIG. 1 is designated generally by the reference character 1 and comprises a U-shaped frame 2 having a pair of spaced apart, generally parallel limbs 3 and 4 joined at corresponding ends by a substantially semicircular connector 5. At the free end of the limb 3 is a large area handle or grip 6 joined to the limb by a stem 7. The area of the grip 6 is sufficient to facilitate the transfer of the tray from one person's hand to another person's hand.

The tray parts thus far described preferably are unitarily molded from an elastomeric material of the kind conventionally used for the making of dental impression trays, such as a moldable glass-filled nylon substance, but any one of a number of readily available materials may be used in the formation of the tray limbs and handle. One suitable impression material adapted for use with the tray is a pliable, putty-like silicone substance which is readily available in the marketplace.

The components of the tray thus far described preferably are molded integrally with a support 8 formed of open mesh netting which spans the limbs 3 and 4. The mesh may be composed of any one of a number of suitable plastic gauzes having fairly uniformly spaced openings 9 therethrough.

Each of the limbs 3 and 4 has an outer or buccal wall 10 which is of such height as to extend both above and below the level of the mesh 8. At the lingual edge of each limb 3 and 4 is a row of projections 11 which, as shown, also extend above and below the level of the mesh 8. The projections 11 are spaced from and free of the adjacent wall 10 by a web 12 which has a plurality of spaced openings 13 extending therethrough.

Each projection 11 is spaced from its adjacent projection by a gap 14. The openings 13 inboard of the ends of each row are positioned adjacent the gap between adjacent projections 11. The openings at the ends of the rows are adjacent, but outboard of, the terminal projections. The mesh 8 preferably is of such size as to span not only the space between the limbs 3 and 4, but also the openings 13.

The construction and arrangement of the impression tray are such that dental impression material (not shown) may be placed in overlying relation on opposite sides of the supporting mesh 8 and in such quantity as to ensure lateral displacement of portions of the material outwardly against the buccal walls 10 when the tray and impression material supported thereby are placed in a patient's mouth and the patient moves his jaw in such manner as to compress the impression material between the upper and lower teeth. As the patient's teeth move into the impression material the latter will be displaced laterally against the buccal walls 3 and 4 as well as against the projections 11. The impression material also will be displaced vertically whereupon the space between the walls 3 and 4 and their adjacent rows of projections, as well as the gaps between adjacent projections will be filled with the dental impression material. In addition, the openings 13 in the webs 12 will be filled with the dental impression material. Those portions of the mesh 8 which span the openings 13 assist in retaining the impression material in such openings.

As the patient's teeth enter the impression material supported by the tray the impression material will be displaced both laterally and vertically, as has been indicated. Laterally outward displacement will be restrained by the buccal walls 10, thereby avoiding excessive lateral displacement of the impression material. The projections 11 also will restrain to some extent inward displacement of the impression material. However, the principal function of the projections and their associated gaps is to prevent or minimize movement of the impression material laterally and longitudinally of the limbs during the setting of the impression material and removal of the tray from a patient's mouth, thereby ensuring a faithful reproduction of the patient's dentition. The filling of the openings 9 and 13 in the mesh 8 and the web 12, respectively, also participates in minimizing any tendency on the part of the impression material to shift its position during the setting of such material.

Once the dental impression material has become set, it nevertheless is elastically pliable so as to permit removal from the patient's mouth without distortion.

The embodiment disclosed in the drawings includes buccal walls and lingual projections which extend both above and below the level of the support mesh 8. However, it is possible to provide and utilize a tray wherein the buccal walls and lingual projections project in one direction only from the level of the mesh. Nevertheless, the interlock between the impression material and the tray provided by the projections, the gaps between the projections, and the openings in the webs ensure appropriate avoidance of shifting of the impression material during the making of the impression and the removal of the hardened or set mold from the patient's mouth.

The tray disclosed in the drawings constitutes a posterior tray. The principles of the invention, however, are equally applicable to quadrant, anterior, sideless, and full arch trays.

The disclosed embodiment is representative of a presently preferred form of the invention, but is intended to be illustrative rather than definitive thereof. The invention is defined in the claims.

I claim:

1. A dental impression tray comprising a frame having limbs spaced apart, each of said limbs having outer and inner edges; a support spanning the inner edges of said limbs and forming a support for dental impression material; an upstanding wall adjacent the outer edge of at least one of said limbs; and a row of projections adjacent the inner edge of said one of said limbs, said projections being spaced from the adjacent wall and from one another, the space between the wall and said projections of said one of said limbs forming a web, said web having a plurality of openings extending therethrough.

2. The tray according to claim 1 wherein said openings are located between adjacent ones of said projections.

3. The tray according to claim 2 wherein others of said openings are located outboard of opposite ends of the associated row.

4. The tray according to claim 1 wherein said wall extends in one direction only from said one of said limbs.

5. The tray according to claim 1 wherein said wall extends in opposite directions from said one of said limbs.

6. The tray according to claim 5 wherein the projections of said row thereof extend in opposite directions from said one of said limbs.

7. The tray according to claim 1 wherein said support is formed by open mesh netting.

8. The tray according to claim 1 including a second limb substantially parallel to said one of said limbs.

9. The tray according to claim 8 wherein said one of said limbs and said second limb are joined at corresponding ends by a connector.

10. The tray according to claim 9 wherein each of said limbs has a thickness greater than that of said connector.

11. The tray according to claim 8 wherein said limbs are substantially parallel to one another.

12. The tray according to claim 1 including a handle attached to and extending from said one of said limbs.

13. The tray according to claim 1 wherein said tray has the configuration of a selected one of a full arch, quadrant, anterior, and posterior dental tray.

14. A dental impression tray comprising a frame having substantially parallel limbs joined at corresponding ends by an arcuate connector, said limbs having free opposite ends, said limbs having outer and inner edges spaced by a web; a support for dental impression material spanning the inner edges of said limbs; and an upstanding wall adjacent the outer edge of each of said limbs, said web being pierced by a plurality of spaced apart openings arranged in a row.

15. The tray according to claim 14 including a row of upstanding projections adjacent the inner edge of each of said limbs, said projections being spaced from one another and from the adjacent wall.

16. The tray according to claim 15 wherein said wall extends beyond the level of said web a distance greater than that of said projections.

17. The tray according to claim 15 wherein selected ones of said openings are located between adjacent ones of said projections and others of said openings are outboard of said row of projections.

18. The tray according to claim 15 wherein said upstanding wall and said projections extend in opposite directions beyond the level of said web.

19. A dental impression tray comprising a frame having limbs spaced apart, each of said limbs having outer and inner edges; a support spanning the inner edges of said limbs and forming a support for dental impression material; an upstanding wall adjacent the outer edge of at least one of said limbs; and a plurality of projections in a row adjacent the inner edge of said one of said limbs, said projections being free from the adjacent wall and spaced from one another by a gap.

20. The tray according to claim 19 wherein the space between the wall and said projections of said one of said limbs forms a web, said web having a plurality of openings extending therethrough.

21. The tray according to claim 20 wherein said openings are located between adjacent ones of said projections.

\* \* \* \* \*